United States Patent
Maekawa et al.

[11] 3,982,946
[45] Sept. 28, 1976

[54] BIS-AZO PYRAZOLONE TYPE DYE DEVELOPER AND LIGHT-SENSITIVE MATERIAL

[75] Inventors: Yukio Maekawa; Seiki Sakanoue, both of Minami-ashigara, Japan

[73] Assignee: Fuji Photo Film Co., Ltd., Minami-ashigara, Japan

[22] Filed: Feb. 10, 1975

[21] Appl. No.: 548,838

[30] Foreign Application Priority Data
Feb. 8, 1974  Japan ............................ 49-16026

[52] U.S. Cl. ........................................ 96/73; 96/3; 96/290; 96/77; 96/99
[51] Int. Cl.² ...................... G03C 1/76; G03C 1/40; G03C 7/00; G03C 1/10
[58] Field of Search ................ 96/290, 3, 77, 99, 73

[56] References Cited
UNITED STATES PATENTS

| | | | |
|---|---|---|---|
| 3,183,090 | 5/1965 | Jarrett | 96/77 |
| 3,236,643 | 2/1966 | Husek | 96/29 D |
| 3,307,947 | 3/1967 | Idelson et al. | 96/77 |
| 3,424,742 | 1/1969 | Jarrett | 96/77 |

*Primary Examiner*—David Klein
*Assistant Examiner*—Richard L. Schilling
*Attorney, Agent, or Firm*—Sughrue, Rothwell, Mion, Zinn and Macpeak

[57] ABSTRACT

A dye developer represented by the following general formula (I):

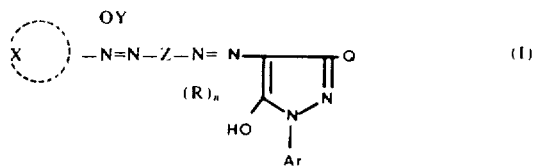

wherein X represents the atoms necessary for completing a monocyclic or polycyclic aromatic group; Y represents an acyl group having 1 to 4 carbon atoms; Ar and Z each represents a monocyclic polycyclic aromatic group, with Ar being connected either directly or through a divalent atom or group to a polyhydric phenol moiety having a silver halide developing action; R represents an alkyl group or an alkoxy group; n represents an integer of 0 to 4; and Q represents

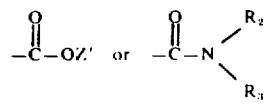

wherein Z' represents a hydrogen atom or an alkyl group, $R_2$ and $R_3$ each represents a hydrogen atom or an aliphatic group, or $R_2$ and $R_3$ can combine to form a divalent aliphatic group and a light-sensitive material comprising a support having thereon a light-sensitive silver halide emulsion layer with the dye developer of this invention associated therewith.

14 Claims, 3 Drawing Figures

BIS-AZO PYRAZOLONE TYPE DYE DEVELOPER AND LIGHT-SENSITIVE MATERIAL

BACKGROUND OF THE INVENTION

1. Field of the Invention

The present invention relates to a dye developer and, more particularly, to a dye developer for a light-sensitive material which can provide an image by a diffusion transfer process. More specifically, the present invention is concerned with a novel cyan dye developer to be used in a color diffusion transfer light-sensitive material, whose absorption is shifted to the short wavelength side upon exposure and is altered to the desired hue upon reaction with a processing solution.

2. Description of the Prior Art

Japanese Patent Publication No. 5189/59 describes a process for forming a transferred dye image using a dye developer. The term "dye developer" as used herein means a compound which possesses both a group capable of developing a silver halide emulsion and a dye moiety, and which is immobilized in accordance with the amount of developed silver halide, the rest being transferred to an image-receiving element to provide a transferred image.

When such a dye developer is associated with a light-sensitive emulsion having a substantial spectral sensitivity in the absorption region of the dye developer and disposed thereon on the side to be exposed with respect to this emulsion or incorporated in the same layer, desensitization of the light-sensitive emulsion apparently occurs due to the light absorption of the dye developer itself. In order to prevent this desensitization, Japanese Patent Publication No. 12393/61 describes a means of chemically modifying the dye developer to initially convert the dye developer to a compound having an absorption shifted toward a shorter wave length and restoring the absorption of reaction with a processing solution upon processing. However, this patent describes only magenta dye developers.

Anthraquinone derivatives, phthalocyanine derivatives and bis-azo derivatives have heretofore been known as cyan dye developers. For example, anthraquinone cyan dye developers are described in detail in U.S. Pat. Nos. 3,135,606, 3,209,016, Japanese Patent Publication Nos. 4380/59, 12432/60 and 17243/63, phthalocyanine dye developers are described in U.S. Pat. No. 3,674,478, and bis-azo cyanine dye developers are described in U.S. Pat. Nos. 3,134,762, 3,236,645, 3,142,565, 3,173,906, etc.

However, these conventional anthraquinone, phthalocyanine or bisazo cyan dye developers reduce the efficiency of active light upon exposure due to a filter effect from the light absorption of the dyes themselves, thus reducing the sensitivity of the light-sensitive material. Also, enhancing the sensitivity of a silver halide emulsion to obtain a highly sensitive light-sensitive material tends to cause a reduction in image density and to make the light-sensitive material itself unstable.

In particular, with conventional bis-azo cyan dye developers, the hue possesses an absorption maximum at not more than about 600 m$\mu$ and therefore a desirable image having an absorption maximum at not less than about 600 m$\mu$ cannot be obtained.

Also, with conventional anthraquinone cyan dye developers, the extinction coefficient of image formation is so low that the optical density tends to be insufficient unless these dye developers are employed in a large amount. On the other hand, conventional anthraquinone and phthalocyanine cyan dye developers have the defect that a slight modification of the chemical structure thereof is difficult and a chemical structure showing optimum photographic properties is difficult to synthesize.

SUMMARY OF THE INVENTION

An object of the present invention is to provide a cyan dye developer having a novel chemical structure, which does not reduce the sensitivity of a light-sensitive material due to the effect of filtering active light by the high absorption of the dye itself.

Another object of the present invention is to provide a dye developer capable of providing a cyan dye image having a high optical density after processing.

A further object of the present invention is to provide a dye developer capable of providing, after processing, a cyan dye image of a desirable hue in a long wavelength region.

Still a further object of the present invention is to provide a cyan dye developer having a chemical structure permitting slight modification with ease so as to obtain optimum photographic properties.

As a result of extensive investigations on cyan dye developers, it has been discovered that the compounds represented by the following formula (I) can attain the above-described objects. In particular, this type of cyan dye developer has the property that, prior to processing, the absorption of these cyan dye developers lies in a short wave-length region and, after processing, their hues are altered to a predetermined hue.

In addition, the cyan dye developers of the present invention of the general formula (I) can provide higher optical density of color images after processing, as compared with conventional anthraquinone cyan dye developers.

The dye developers of the present invention are represented by the following general formula (I):

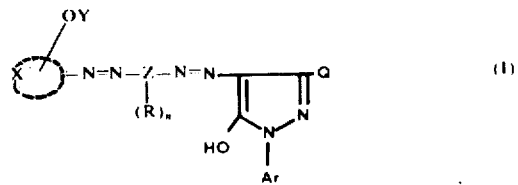

wherein X repesents the atoms necessary for completing a monocyclic or polycyclic aromatic group; Y represents an acyl group having 1 to 4 carbon atoms; Ar and Z each represents a monocyclic or polycyclic aromatic group, Ar being connected either directly or through an atom or atoms to a polyhydric phenol having a silver halide developing action; R represents an alkyl group or an alkoxy group; n represents an integer of 0 to 4; and Q represents

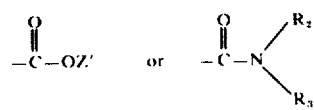

wherein Z' represents a hydrogen atom or an alkyl group, $R_2$ and $R_3$ each represents a hydrogen atom or an aliphatic group, or $R_2$ and $R_3$ can combine with each other to form a divalent aliphatic group.

DETAILED DESCRIPTION OF THE INVENTION

Figure 1:
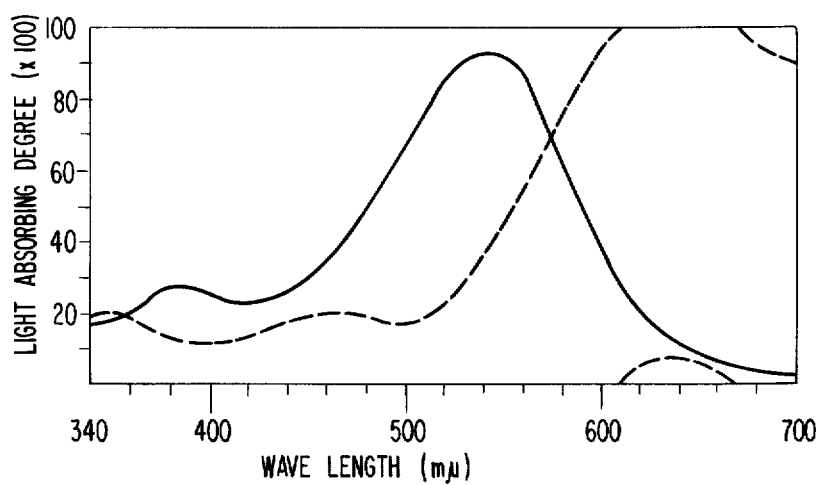
FIG. 1 is a graph comparatively showing the spectral absorption of Compound 1 in acetone (solid line) and that in acetone containing an alkali (broken line).

The dye developers represented by the foregoing general formula are described in detail below.

As the atom group completed by X in the general formula (I), a naphthalene nucleus is generally employed. In addition, suitable examples of nuclei completed by X include a benzene nucleus, a coumarone nucleus, an indole nucleus, a benzothiophene nucleus, a quinoline nucleus, an oxazole nucleus, a thiazole nucleus, a naphthyridine nucleus, and the substituted derivatives thereof. Examples of substituents present in such substituted derivatives are an alkyl group (preferably having 1 to 4 carbon atoms such as a methyl group, an ethyl group, a propyl group, an isopropyl group, an n-butyl group, and a tert-butyl group), a sulfo group, an alkoxy group (preferably having 1 to 4 carbon atoms such as a methoxy group, an ethoxy group, a propoxy group, an isopropoxy group, an n-butoxy group, and a tert-butoxy group), an aryl group (including a monocyclic or fused polycyclic aromatic group, e.g., a phenyl group, a naphthyl group, etc.), an aryloxy group (the aryl moiety being the same as described with respect to the above-described aryl group), an amino group, a carboxy group, an alkylamino group (having 1 to 4 carbon atoms in the alkyl moiety with suitable alkyl moieties corresponding to the alkyl groups described above), an arylamino group (the aryl moiety being the same as described with respect to the above-described aryl group), a hydroxy group, a cyano group, an alkylamido group (having 1 to 4 carbon atoms in the alkyl moiety with suitable alkyl moieties corresponding to the alkyl groups described above), an arylsulfonamido group (the aryl moiety being the same as described with respect to the above-described aryl group), and the like. Y represents an acyl group having 1 to 4 carbon atoms such as a formyl group, an acetyl group, a propionyl group, and a butyryl group. In particular, an acetyl group is inexpensive and generally advantageous. Acyl groups having 1 to 4 carbon atoms (as described above) and substituted with a hydroxy group, a carboxy group, etc. are advantageous for increasing the transfer property. Also, acyl groups having 1 to 4 carbon atoms and substituted with a chlorine atom, a bromine atom, an alkoxy group (preferably having 1 to 4 carbon atoms and as described above), etc. are advantageous for adjusting the color-recovery speed. Ar and Z each represents a monocyclic or polycyclic aromatic group which may be substituted which substituents which do not affect the characteristics thereof. For example, a benzene nucleus and a naphthalene nucleus are peferred. Ar is connected, either directly or through an atom or atoms with an alkylene group (e.g., —CH$_2$—, —CH$_2$CH$_2$—, etc.), —O—, —S—, —SO$_2$—, —CO—, —COCH$_2$—, and —CH$_2$CH$_2$S— being particularly preferred, to a polyhydric phenol having a silver halide developing action such as a 2,5-dihydroxyphenyl group, 2,3-dihydroxyphenyl group, or 3,4-dihydroxyphenyl group. R represents an alkyl group or an alkoxy group preferably having 1 to 4 carbon atoms. For example, suitable examples of alkyl groups and alkoxy groups are a methyl group, an ethyl group, a methoxy group, an ethoxy group, etc., as described above, n represents an integer of 0, 1, 2 or 4, and the R's can be the same or different from each other. Q represents

wherein Z' represents a hydrogen atom or an alkyl group (having 1 to 12, preferably 1 to 6, carbon atoms), and $R_2$ and $R_3$ each represents a hydrogen atom or an aliphatic group or can be combined with each other to form a divalent aliphatic group (such as —CH$_2$)$_5$—, —(CH$_2$)$_2$—O—(CH$_2$)$_2$—, etc.).

From the standpoint of silver halide development activity of the polyhydric phenol, the connection between Ar and a polyhydric phenol having a silver halide developing action is desirably such that Ar is connected to the polyhydric phenol moiety either directly or through one or more methylene groups, although this is not an essential characteristic of the invention.

Specific examples of the compounds of the general formula (I) of the present invention are illustrated below.

Compound 1

1-[4'-(Hydroquinonylethyl)phenyl]-3-carboxy-4-[2″,5″-dimethoxy-4″-(1‴-acetoxy-4‴-isopropoxynaphthyl-2‴-azo)phenylazo]-5-pyrazolone

Compound 2

1-[4'-(Hydroquinonylethyl)phenyl]-3-carboxy-4-[3″-methoxy-4″-(1‴-acetoxy-4‴-isopropoxynaphthyl-2‴-azo)phenylazo]-5-pyrazolone

Compound 3

1-[4'-(Hydroquinonylethyl)phenyl]-3-carboxy-4-[2″-methoxy-4″-(1‴-acetoxy-4‴-isopropoxynapthyl-2‴-azo)phenylazo]-5-pyrazolone

Compound 4

1-[4'-(Hydroquinonylethyl)phenyl]-3-carboxy-4-{2″,5″-dimethoxy-4″-[1‴-acetoxy-4‴-[(2-methoxy)ethoxy]naphthyl-2‴-azo]phenylazo}-5-pyrazolone

Compound 5

1-[4'-(Hydroquinonylethyl)phenyl]-3-ethoxycarbonyl-4-[2″,5″-dimethyl-4″-(1‴-chloroacetoxy-4‴-isopropoxynapthyl-2‴-azo)phenylazo]-5-pyrazolone

Compound 6

1-[4'-(Hydroquinonylethyl)phenyl]-3-methoxycarbonyl-4-[2″,5″-diethoxy-4″-(1‴-acetoxy-4‴-

[(2-ethoxy)ethoxy]-naphthyl-2'''-azo)phenylazo]-5-pyrazolone

Compound 7

1-[3'-(Hydroquinonylmethyl)phenyl]-3-carboxy-4-[2'',5''-dimethoxy-4''-(1'''-acetoxy-4'''-isopropoxynaphthyl-'''-azo)phenylazo]-5-pyrazolone

Compound 8

1-[2'-(Hydroquinonyl)phenyl]-3-carboxy-4-[(2'',5''-dimethoxy-4''-(1'''-acetoxy-4'''-isopropoxynaphthyl-2'''-azo)phenylazo]5-pyrazolone

Compound 9

1-[4'-(Hydroquinonylethyl)phenyl]-3-carbamoyl-4-[2'', 5''-dimethoxy-4''-(3'''-acetoxybenzo[b]thienyl-2'''-azo)phenylazo]-5-pyrazolone

Compound 10

1-[4'-(Hydroquinonylethyl)phenyl]-3-N,N-cyclopentamethylenecarbomoyl-4-[2',5'-dimethoxy-4'-(6''-methoxyacetoxyquinolyl-5''-azo)-phenylazo]-5-pyrazolone Azo dyes can essentially assume hydrazine tautomeric forms in which they exhibit an absorption in a longer wavelength region and an azo form in which they exhibit an absorption in a shorter wavelength region.

Since the dye developers of the present invention are fixed in an azo-type tautomeric from by acylation as illustrated above as the examples, they exhibit an absorption in a short wavelength region. However, it appears that upon reaction with a processing solution after exposure, the acyl group is eliminated to form a hydroxy group and the proportion of the hydrazine type tautomer increases, resulting in the absorption being shifted to a longer wavelength side.

The compounds of the present invention represented by the general formula (I) can be synthesized according to the following process.

First, a monocyclic or polycyclic aromatic compound having a nitro group and an amino group of the general formula (II)

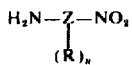
(II)

wherein Z, R and n are the same as hereinbefore defined is diazotized in a conventional manner as disclosed in U.S. Pat. Nos. 3,230,085 and 3,236,645 (for example; with sodium nitrite and hydrochloric acid), and then subjected to a coupling reaction with a monocyclic or polycyclic aromatic coupler to obtain a compound of the general formula (III)

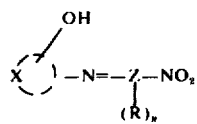
(III)

wherein X, Z, R and n are the same as defined hereinbefore. This compound is then reduced to convert the nitro group to an amino group in a conventional reduction, e.g., as disclosed in U.S. Pat. Nos. 3,019,107 and 3,236,893 (for example, (1) by using a suitable reducing agent such as stannous chloride in various organic solvents (e.g., ethyl alcohol, etc.), or (2) by conducting a catalytic reduction using hydrogen and a palladium-carbon catalyst), thus obtaining compound of the general formula (IV)

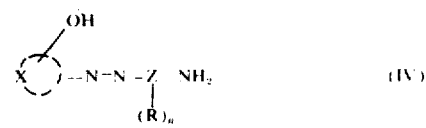
(IV)

where X, Z, R and n are the same as defined hereinbefore.

The compound of the general formula (IV) is diazotized in a conventional manner (e.g., with sodium nitrite and glacial acetic acid) and, after coupling with a compound of the general formula (IV), the hydroquinone OH group in the compound of the general formula (V) structure moiety protected with an acyl group is hydrolyzed under an oxygen-free condition (for example, by processing with potassium hydroxide in ethanol in vacuo and acidifying with hydrochloric acid as disclosed in U.S. Pat. Nos. 3,134,672 and 3,134,764) to obtain a compound (VI)

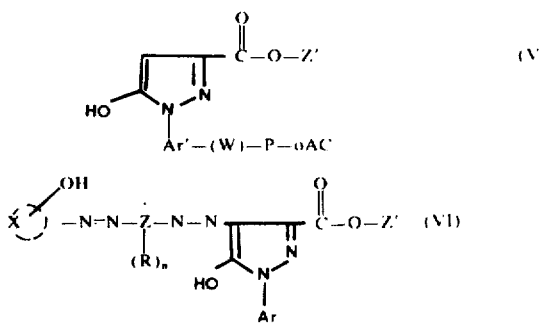

wherein Ar and Z' are the same as mentioned before, Ar' represents a monocyclic or polycyclic aromatic group, P-oAC represents an acylated polyhydric phenol and W represents a linkage where Ar' and P-oAC are not directly connected to each other. Additionally, a process for synthesizing the compound of the general formula (V) is described in detail in U.S. Pat. No. 3,252,990. With the compound of the general formula (VI), it is also possible to convert the ester group in the 3-position of the pyrazolone to a carboxamido group by reacting this compound with a suitable amine as described in U.S. Pat. No. 3,141,772. Therefore, the compound of the general formula (VI) can be represented as follows including these carboxamido derivatives;

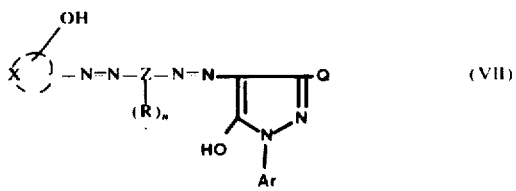
(VII)

wherein Q represents —COOZ' or

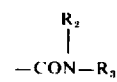

with Z′, R₂ and R₃ being the same as described before.

The novel dye developers represented by the general formula (I) can be obtained by oxidizing the polyhydric phenol moiety of the compound of the general formula (VII) in a solvent (e.g., a mixture of ethylene dichloride and dimethylformamide) using an oxidizing agent (e.g., p-benzoquinone, manganese dioxide, etc.), conducting acylation using an acylating agent (e.g., isopropenyl acetate, a substituted or unsubstituted carboxylic acid halide, etc), and reducing the oxidized polyhydric phenol moiety using a reducing agent (e.g., 2,5-di-t-butyl-hydroquinone, N,N-diethylhydroxylamine, etc.) or by a catalytic reduction with hydrogen using palladium-carbon or the like to thereby restore the polyhydric phenol form, e.g., as disclosed in U.S. Pat. Nos. 3,086,005 and 3,307,947.

The dye developer of the present invention is generally dispersed in a carrier, hydrophilic colloid, according to the following method. That is, the dye developer is dissolved in an organic solvent, and the resulting solution is added to a hydrophilic colloid solution and dispersed therein as fine droplets. Where easily evaporatable solvents such as ethyl acetate, tetrahydrofuran, methyl ethyl ketone, etc. are used, these solvents can be removed in a step of drying photographic layers or according to the method described in U.S. Pat. Nos. 2,322,027 and 2,801,171. Solvents which are easily readily soluble in water such as dimethylformamide, 2-methoxyethanol, etc., can be removed by washing with water according to the method described in U.S. Pat. Nos. 2,949,360, 3,396,027, etc. However, in order to stabilize the dispersion of the dye developer and accelerate the dye image-forming step, it is advantageous to incorporate the dye developer in a solvent which is substantially insoluble in water and having a boiling point of not less than about 200°C at ordinary pressure. Examples of high boiling solvents are dibutyl, phthalate, tricresyl phosphate, trihexyl phosphate, N,N-diethyllaurylamide, etc. In order to accelerate the dissolution of the dye developer, it is desirable to use the above-described volatile or water-soluble solvents as auxiliary solvents.

Furthermore, an oleophilic polymer can be used in place of or in addition to the high boiling solvent. Examples of oleophilic polymers which can be used are, for example, a polyester resin obtained by the polycondensation of a polyhydric alcohol and a polycarboxylic acid. Polymers other than this which can be used can be selected from polyvinyl pyrrolidone, polyvinyl acetate, polyvinyl propionate, polyvinyl butyral, polyvinyl chloride, polyacrylate, polymethacrylate, nitrocarboxymethyl cellulose, N-vinylpyrrolidone-acrylic acid copolymers, N-vinyl pyrrolidone-acrylic acid-methyl acrylate copolymers, vinyl phthalamide-acrylic acid copolymers, cellulose acetate hydrogen phthalate, poly-N-methylmethacrylamide, dimethylaminoethylmethacrylate-acrylic acid copolymers, dimethylaminoethylmethacrylateacrylic acid-butyl acrylate copolymers, N,N-diethylacrylamideacrylamide copolymers, poly-N-methylacrylamide copolymers, N-methylacrylamide-N-hydroxymethyl-acrylamide copolymers, poly-N-ethylacrylamide, methyl vinyl ketone-acrylamide copolymers and N-vinylpyrrolidone-methacrolein copolymers.

In general, in dispersing the solution as fine droplets, a colloid mill, a high pressure homogenizer, an ultrasonic wave emulsifying apparatus, and the like are employed. Also, anionic surface active agents (mainly anionic type) are preferably used as an emulsifying aid.

Illustrative examples of hydrophilic colloids to be used for dispersing the dye developer are gelatin, colloidal albumin, casein, cellulose derivatives (e.g., carboxymethyl cellulose, hydroxyethyl cellulose, etc.), saccharide derivatives (e.g., agar-agar, sodium alginate, starch derivatives, etc.), synthetic hydrophilic colloids (e.g., polyvinyl alcohol, poly-n-vinyl pyrrolidone, polyacrylic acid copolymers, polyacrylamide, the derivatives or partially hydrolyzed products thereof, etc.). If desired, a compatible mixture of two or more of these hydrophilic colloids can be used. The most generally used hydrophilic colloid is gelatin. Gelatin can be replaced, partly or completely, by a synthetic high molecular weight substance, by a so-called gelatin derivative (prepared by processing and modifying gelatin with a compound having a group capable of reacting with the functional groups contained in the gelatin molecule (i.e., amino groups, imino groups, hydroxy groups or carboxy groups)), or by a graft polymer prepared by grafting a molecular chain of another high molecular weight substance onto the gelatin molecule. Examples of compounds for preparing the gelatin derivatives are, e.g., the isocyanates, acid chlorides and acid anhydrides as described in U.S. Patent 2,614,928, the acid anhydrides as described in U.S. Patent 3,118,766, bromoacetic acid as described in Japanese Patent Publication No. 5514/64, the phenyl glycidyl ethers as described in Japanese Patent Publication No. 26845/67, the vinyl sulfone compounds as described in U.S. Pat. No. 3,132,945, the N-allylvinylsulfonamides as described in British Patent 861,414, the maleinimide compounds as described in U.S. Pat. No. 3,186,846, the acrylonitriles as described in U.S. Pat. No. 2,594,293, the polyalkylene oxides described in U.S. Pat. No. 3,312,553, the epoxy compounds described in Japanese Patent Publication No. 26845/67, the acid esters as described in U.S. Pat. No. 2,763,639, the alkanesulfones as described in British Patent 1,033,189, and the like. As to the branch high polymers to be grafted onto gelatin, many descriptions are given in U.S. Pat. Nos. 2,763,625, 2,831,767, 2,956,884, Polymer Letters, 5, 595 (1967), Photo. Sci. Eng., 9, 148 (1965), J. Polymer Sci., A-1, 9, 3199 (1971), and the like. Homopolymers or copolymers of those monomers which are generally called vinyl monomers, such as acrylic acid, methacrylic acid, the ester, amide or nitrile derivatives, thereof, styrene, etc. can be widely used. However, hydrophilic vinyl polymers having some compatibility with gelatin, such as homopolymers of acrylic acid, acrylamide, methacrylamide, hydroxyalkyl acrylates, hydroxyalkyl methacrylates, etc. are particularly preferred.

When the dye developer is used together with an auxiliary developing agent, the dye developer of the present invention can provide a color diffusion transfer image having particularly preferred photographic properties. Suitable auxiliary developing agents which can be used are those which are already known as auxiliary developing agents such as hydroquinone derivative, a catechol derivative, a 1-phenyl-3-pyrazolidone derivative, etc. Specific examples are described in British Pat. No. 1,243,539, U.S. Pat. No. 3,253,915, Belgian Pat. No. 722,298, French Patent 1,599,790, Japanese Pat.

Publication Nos. 29130/64, 13837/68, etc. For example the following auxiliary developing agents can be used: phenylhydroquinone, 2'-hydroxyphenylhydroquinone, phenoxyhydroquinone, 4'-methylphenylhydroquinone, 1,4-dihydroxynaphthalene, 2-(4-aminophenethyl)-5-bromohydroquinone, 2-(4-aminophenethyl)-5-methylhydroquinone, 4'-aminophenethylhydroquinone, 2,5-dimethoxyhydroquinone, 2,5-dibutoxyhydroquinone, m-xylohydroquinone, bromohydroquinone, 3,6-dichlorohydroquinone, 2-dimethylaminomethyltoluhydroquinone, 2-cyclohexylhydroquinone, sec-butyl-hydroquinone, 2,5-dichlorohydroquinone, 2,5-diisopropylhydroquinone, 2,5-diiodohydroquinone, 3-chlorotoluhydroquinone, tetrachlorohydroquinone, 2,5-diphenylhydroquinone, 2,5-diresorcylhydroquinone, 2,5-dioctylhydroquinone, dodecylhydroquinone, 4-methoxycatechol, 4-isopropoxycatechol, 3-isopropylcatechol, 4-phenylcatechol, 3,6-dimethylcatechol, 1,2-dihydroxy-5,8-methanol-5,6,7,8-tetrahydronaphthalene, etc.

In addition to these auxiliary developing agents, for example, hydroquinone and the derivatives thereof having substantially sufficient solubility in water together with the dye developer can be used. Typical examples of hydroquinones having substantially sufficient solubility in water, which can be used, are, e.g., hydroquinone, hydroxyhydroquinone, chlorohydroquinone, methylhydroquinone, methoxyhydroquinone, hydroxymethylhydroquinone, aminohydroquinone hydrochloride, 2,5-diaminohydroquinone hydrochloride, aminomethylhydroquinone hydrochloride, aminoethylhydroquinone hydrobromide, 2,5-dihydroxythiophenol, etc.

Furthermore, examples of other auxiliary developing agents which can be used are quinone and the derivatives thereof. For example, benzoquinone, phenylbenzoquinone, 4'-methylphenylbenzoquinone, 2,3,5-trimethylbenzoquinone, 1,4-naphthoquinone, 2,5-dimethoxybenzoquinone, 2,6-dimethylbenzoquinone, bromobenzoquinone, 2,5-dichlorobenzoquinone, cyclohexylbenzoquinone, 2,5-di-n-butylbenzoquinone, p-chlorotoluquinone, toluquinone, 2,5-diphenylbenzoquinone, dodecylbenzoquinone, 2,6-diiodobenzoquinone, fluorobenzoquinone, 2,5-diallylbenzoquinone, 2'-chlorophenylbenzoquinone, 3'-nitrophenylbenzoquinone, benzylbenzoquinone, etc., can be used.

In addition to these auxiliary developing agents, also polyhydroxybenzene derivatives, amyl gallate described in Japanese Patent application No. 124916/72, spiro compounds described in Japanese Patent Application No. 82274/72 and 125611/72 can be used.

In a light-sensitive element for use in the color diffusion transfer process, a silver halide emulsion and a dye developer are associated with each other. A suitable amount of the dye developer ranges from about 0.3 to 10 mols, preferably 2 to 10 mols, per mol of the silver halide.

The silver halide emulsion to be used in the present invention is a hydrophilic colloidal dispersion of silver chloride, silver bromide, silver chlorobromide, silver bromoiodide, silver chlorobromoiodide or a mixture thereof. The halide composition is selected depending upon the end use purpose of the light-sensitive material and the processing conditions. In particular, a silver bromoiodide emulsion or silver chlorobromoiodide emulsion containing about 1 mol% to 10 mol% iodide, not more than about 30 mol% chloride and the balance bromide is desirable. The silver halide grains to be used can be an ordinary size or a fine size and, preferably, those which possess a mean grain size of about 0.1 $\mu$ to about 2 $\mu$ are preferred. For some end-use purposes of the light-sensitive material, silver halides having a uniform grain size are desirable. The grains to be used can be in a cubic form, an octahedral form or in a mixed crystal form. These silver halide emulsions can be prepared according to the known conventional processes as described in P. Grafkides; Chimie Photographique, 2nd Ed. Chapters 18 to 23, Paul Montel, Paris (1957). That is, a soluble silver salt such as silver nitrate and a water soluble halide such as potassium bromide are reacted with each other in the presence of a solution of a hydrophilic protective colloid such as gelatin and crystals are allowed to develop in the presence of excess halide or of a solvent for the silver halide such as ammonia. In this occasion, a single or double jet method or a pAg-controlled double method can be employed as the precipitating method. Removal of the soluble salts from the emulsion can be effected by washing and dialysis of the cool-set emulsion, by the combination of the addition of a sedimenting agent such as an anionic polymer having sulfone groups, sulfuric ester groups or carboxy groups or an anionic surface active agent and the adjustment of pH, or by the combination of the use of an acylated protein such as phthaloyl gelatin as a protective colloid and the adjustment of pH, to thereby cause sedimentation.

The silver halide emulsions to be used in the present invention are preferably subjected to chemical sensitization employing a heat-treatment using the natural sensitizers contained in gelatin, a sulfur sensitizer such as sodium thiosulfate or N,N,N'-trimethylthiourea, a gold sensitizer such as a thiocyanate complex salt or thiosulfate complex salt of monovalent gold, or a reducing sensitizer such as stannous chloride or hexamethylenetetramine. Also, emulsions which are tend to form a latent image on the surface of the silver halide grains and emulsions which tend to form a latent image inside the silver halide grains as described in U.S. Pat. Nos. 2,592,550, 3,206,313, etc. can be used in the present invention.

The silver halide emulsions to be used in the present invention can be stabilized with additives such as 4-hydroxy-6-methyl-1,3,3a,7-tetrazaindene, 5-nitroimidazole, 1-phenyl-5-mercaptotetrazole, 8-chloromercuriquinoline, benzenesulfinic acid, pyrocatechin, 4-methyl-3-sulfoethylthiazolidin-2-thione, 4-phenyl-3-sulfoethylthiazolidine-2-thione, etc. In addition, inorganic compounds such as cadmium salts, mercury salts, complex salts of platinum group metals such as the chloro complex salt of palladium, and the like are also useful for stabilizing the light-sensitive material of the present invention. Furthermore, the silver halide emulsions to be used in the present invention can contain sensitizing compounds such as a polyethylene oxide compound.

The silver halide emulsions to be used in the invention can possess, if desired, a color sensitivity expanded with optical sensitizing dyes. Useful optical sensitizing agents are cyanines, merocyanines, holopolar cyanines, styryls, hemicyanines, oxanols, hemioxanols, and the like. Specific examples of optical sensitizing agents are described in P. Glafkides, supra, chapters 35 to 41, and F. M. Hamer; The Cyanine Dyes and Related Compounds (Interscience). In particular, cyanines in which a nitrogen atom in a basic hetero ring nucleus is substituted with an aliphatic group (e.g., an alkyl group having a hydroxy group, a carboxy group or a sulfo group), e.g., those described in U.S. Pat. Nos. 2,503,776, 3,459,553 and 3,177,210, are especially useful for the practice of the present invention.

The light-sensitive element of the color diffusion transfer light-sensitive material in accordance with the present invention is coated on a planar substance which does not undergo serious dimensional change during processing, such as a cellulose nitrate film, a cellulose acetate film, a cellulose acetate butyrate film, a cellulose acetate propionate film, a polystyrene film, a polyethylene terephthalate film, a polycarbonate film, the laminates thereof, a thin glass film or the like, which is used for conventional photographic light-sensitive materials. A suitable coating amount on the support ranges from about 0.2 to 30 g (as silver)/m² of the support.

Where the adhesion between the support and the photographic emulsion layer is insufficient, a layer having an adhesive property for both of the support and the emulsion layer can be provided as a subbing layer. Also, in order to further improve the adhesiveness, the surface of the support can be subjected to a preliminary processing such as a corona discharge, irradiation with ultraviolet light, flame processing, or the like.

In the color diffusion transfer light-sensitive element to which the present invention is applicable, a dye developer is associated with a silver halide emulsion. The combination of the color sensitivity of the silver halide emulsion and the spectral absorption of the dye image is appropriately selected depending upon the intended color reproduction. In the reproduction of natural colors according to subtractive color photography, a light-sensitive element having at least two combinations of silver halide emulsions having a selective spectral sensitivity in certain wavelength regions with compounds capable of providing dye images having selective spectral absorptions in the same wavelength region is used. In particular, a light-sensitive element having the combination of a blue-sensitive silver halide emulsion with a compound capable of providing a yellow dye image, the combination of a green-sensitive silver halide emulsion with a compound capable of providing a magenta dye image, and the combination of a red-sensitive silver halide emulsion with a compound capable of providing a cyan dye image is useful. In the light-sensitive element, these combination units of emulsions and dye developers are coated as layers in a face-to-face alignment or coated as one layer by forming each into particles and mixing. In a preferred multi-layered structure, a blue-sensitive silver halide emulsion, a green-sensitive silver halide emulsion and a red-sensitive silver halide emulsion are positioned in sequence from the side to be exposed. In particular, in the case of high speed emulsions containing silver iodide, a yellow filter layer can be positioned between the blue-sensitive silver halide emulsion and the green-sensitive silver halide emulsion. This yellow filter layer contains a yellow colloidal silver dispersion, an oil-soluble yellow dye dispersion, an acidic dye mordanted with a basic polymer, or a basic dye mordanted with an acidic polymer. The emulsion layers are advantageously separated from each other by an interlayer. The interlayer prevents disadvantageous mutual interactions from occurring between emulsion units having different color sensitivities. The interlayer comprises a polymer containing fine pores formed by a latex of a hydrophilic polymer and hydrophobic polymer, as described in U.S. Pat. Nos. 3,625,685 or a polymer whose hydrophilicity is gradually increased by the processing composition, such as calcium alginate, as described in U.S. Pat. No. 3,384,483, as well as a hydrophilic polymer such as gelatin, polyacrylamide, a partially hydrolyzed product of polyvinyl acetate, etc.

The light-sensitive element described in detail above is superposed on an image-receiving element to be described hereinafter in a face-to-face relationship, and processed in general by spreading an alkaline processing solution also to be described hereinafter between these two elements. In this case, the image-receiving element can be either delaminated after transfer processing or can be designed to be viewed as such without delamination by using a transparent support for the image-receiving layer and providing a reflective layer between the image-receiving layer and the light-sensitive layer.

The image-receiving element necessarily possesses a mordanting layer comprising a poly-4-vinyl pyridine latex (particularly in polyvinyl alcohol), polyvinyl pyrrolidone, a polymer containing a quaternary ammonium group as described in U.S. Pat. No. 3,239,337, or the like. A suitable thickness for the mordanting layer can range from about 1 to 100 $\mu$, preferably 5 to 20 $\mu$. In addition, the image-receiving element to be used in the present invention preferably possesses the function of neutralizing alkali brought in by the processing composition. The processing composition contains alkali sufficient to provide a pH of higher than about 10, preferably higher than 11, which is sufficiently high to accelerate the image-forming step comprising the development of the silver halide emulsion and the diffusion of the dye developer. After the substantial completion of the formation of the diffusion transferred images, the pH in the film unit is reduced to around neutrality, i.e., less than about 9, preferably less than 8, whereby further image-formation is actually discontinued to prevent the image tone from changing with the lapse of time and to control discoloration and fading of the images and stains of white background due to the high alkalinity. For this purpose, it is advantageous to provide in the film unit a neutralizing layer containing an acidic substance in a sufficient quantity to neutralize the alkali contained in the processing composition to the above described pH, that is, in an area concentration equivalent to or greater than the amount of the alkali contained in the spread processing composition. Preferred acidic substances are those which contain an acidic group having a pKa of less than about 9 (particularly a carboxy group, a sulfonic acid group, or a precursor group capable of providing such an acidic group upon hydrolysis). More preferable examples are higher fatty acids such as oleic acid described in U.S. Pat. No. 2,983,606, polymers of acrylic acid, methacrylic acid or maleic acid, the partially esterified polymers thereof, or acid anhydrides. Specific illustrative examples of high molecular weight acidic substances are copolymers of a vinyl monomer (e.g., ethylene, vinyl acetate, vinyl methyl ether, etc.) and maleic anhydride, and the n-butyl half ester thereof; copolymers of butyl acrylate and acrylic acid; cellulose acetate-hydrogen phthalate; and the like. In addition to these acidic substances, the neutralizing layer can contain polymers such as cellulose nitrate and polyvinyl acetate, and a plasticizer as described in U.S. Pat. No. 3,557,237. Furthermore, the neutralizing layer can be hardened through a cross linking reaction with a multifunctional aziridine compound, epoxy compound, etc. The neutralizing layer is positioned in the image-receiving element and/or the light-sensitive element. In particular, the neutralizing layer is advantageously positioned between the support of the image-receiving element and the image-receiving layer. As is described in German Pat. OLS 2,038,254, the acidic substances can be microencapsulated for incorporation into the film unit. A suitable thickness of the neutralizing layer can range from about 5 to 20 $\mu$, preferably 10 to 50 $\mu$.

The neutralizing layer or the acidic substance-containing layer to be used in the present invention is desirably separated from the spread processing composition layer by a neutralization rate-controlling layer or timing layer. This timing layer functions to prevent a disadvantageous reduction in the transfer image density due to a too fast reduction in pH before the necessary development of the silver halide emulsion layer and the formation of the diffusion transfer image are completed. That is, the timer layer functions to delay the reduction in pH until the necessary development and transfer are completed.

In a preferred embodiment of the present invention, the image-receiving element possesses a multi-layered structure comprising a support— a neutralizing layer— a timing layer— a mordant layer (image-receiving layer) in this sequence. The timing layer comprises mainly polymers such as gelatin, polyvinyl alcohol, polyvinyl propyl ether, polyacrylamide, hydroxypropylmethyl cellulose, isopropyl cellulose, partially butyrylated polyvinyl alcohol, partially hydrolyzed polyvinyl acetate, a copolymer of $\beta$-hydroxyethyl methacrylate and ethyl acrylate, and the like. These polymers are usefully hardened through a cross linking reaction with an aldehyde compound such as formaldehyde or an N-methylol compound. The timing layer preferably has a thickness of about 2 $\mu$ to 20 $\mu$.

The processing composition to be used in the present invention is a liquid composition containing the processing components necessary for the development of the silver halide emulsion and necessary for the formation of the diffusion transferred dye image. The main solvent therein is water and, in some cases, hydrophilic solvents such as methanol or 2-methoxyethanol are additionally employed. The processing composition contains alkali in a sufficient amount to maintain the pH at the level necessary for causing the development of the emulsion layer and to neutralize acids (e.g., hydrohalic acids such as hydrobromic acid, carboxylic acids such as acetic acid, and the like) to be produced during the various steps of development and dye image formation. Examples of alkalis are alkali metal hydroxides or alkaline earth metal hydroxides such as lithium hydroxide, sodium hydroxide, potassium hydroxide, calcium hydroxide dispersion, etc., tetramethylammonium hydroxide, sodium carbonate, trisodium phosphate, amines such as diethylamine, etc. The processing composition preferably contains an alkali hydroxide in such a concentration that the pH thereof is not less than about 12, in particular not less than 14, at room temperature. More preferably, the processing composition contains a hydrophilic polymer such as high molecular weight polyvinyl alcohol, hydroxyethyl cellulose, sodium carboxymethyl cellulose or the like. These polymers impart to the processing composition a viscosity of not less than about 1 poise, preferably from about several hundred (500 – 600) to about 1,000 poise, at room temperature (about 20° – 30°C), which not only facilitates the uniform spreading of the composition upon processing but also forms, upon concentration of the processing composition due to migration of the aqueous solvent into the light-sensitive element and the image-receiving element in the course of the processing, an immovable film, thus serving to unify the film unit after processing. In addition, this polymer film can serve, after the substantial completion of the formation of the diffusion transferred dye image, to control further migration of the coloring ingredients into the image-receiving layer, thereby preventing the image from being changed.

The processing composition used in the present invention is advantageously retained in a rupturable container. Such a container is advantageously produced by folding a sheet of a liquid- and air-impervious substance and sealing each edge to form a cavity in which the processing composition is retained, and the container is advantageously formed so that, when the film unit passes through pressure-applying members, the container is ruptured at a given portion due to the inner hydraulic pressure generated within the processing composition to thereby release the contents. Suitable advantageous materials for forming the container are a polyethylene terephthalate polyvinyl alcohol/polyethylene laminate, a lead foil/vinyl chloride-vinyl acetate copolymer laminate or the like. This container is desirably fixedly positioned and extends transverse a leading (i.e., in the direction of travel of the film unit with respect to the pressure applying members) edge of the film unit thereby to effect a substantially unidirectional discharge of the contents of the container on the surface of the light-sensitive element. Preferred examples of such containers are described in U.S. Pat. Nos. 2,543,181; 2,643,886; 2,653,732; 2,723,051; 3,056,491; 3,056,492; 3,152,515 and 3,173,580. These containers are advantageous for the practice of the present invention.

In some cases, the processing composition advantageously contains a light absorbent such as carbon black and a desensitizer described in U.S. Pat. No. 3,589,333 so as to prevent the silver halide emulsion from being fogged by ambient light during processing, e.g., outside a camera.

In the color diffusion transfer process, it is desirable to conduct the development processing in the presence of a diffusible onium compound. Examples of such onium compounds are quaternary ammonium compounds, quaternary phosphonium compounds and quaternary sulfonium compounds. Examples of particularly useful onium compounds include 1-benzyl-2-picolinium bromide, 1-(3-bromophenyl)-2-picolinium p-toluenesulfonate, 1-phenethyl-2-picolinium bromide, 2,4-dimethyl-1-phenethylpyridinium bromide, $\alpha$-picoline-$\beta$-naphthoylmethyl bromide, N,N-diethylpiperidinium bromide, phenethylphosphonium bromide, dodecylidimethylsulfonium p-toluenesulfonte, etc. The onium compounds are desirably incorporated in the alkaline processing composition. The onium compound is most preferably employed in a proportion of about 2 to 15% by weight of the total processing composition. The image quality of the transferred images is markedly enhanced by development processing in the presence of the onium compound. Examples of onium compounds other than those illustrated above and their method of use are described in detail in U.S. Pat. Nos. 3,411,904 and 3,173,786. To the processing solution composition can further be added a restrainer such as benzotriazole.

The dye developer of the present invention is used for diffusion transfer light-sensitive materials. For example, the dye developer of the present invention is applicable to a light-sensitive material of the type that an image-receiving element is to be delaminated from a negative element after transfer processing for viewing and, in particular, is useful for a light-sensitive material which permits viewing without delamination as is described in Japanese Patent Publication No. 16356/71. In particular, a non-delamination-type light-sensitive material which permits viewing from the opposite side to the exposed side is excellent as compared with a light-sensitive material of the type which permits viewing from the exposed side in that optical inversion in a camera is not necessary. In order to attain preferred color separation, it is particularly useful to dispose an image-receiving layer, a space where an processing solution is to be spread, a blue-sensitive silver halide emulsion layer and a yellow dye developer-containing hydrophilic colloidal layer in this sequence, and to use a temporarily short-shifted dye developer since it is extremely important to expose a material from the side nearer a dye developer-containing layer.

Some of the effects and advantages obtained by the present invention are enumerated below.

Firstly, since the light absorption of the dye developer itself lies in a short wavelength region upon exposure before processing, a reduction in efficiency of active light due to the filter effect of the dye itself is small. Therefore, a highly sensitive light-sensitive material can be obtained by using the dye developer of the present invention.

Secondly, since loss of light due to the filter effect is prevented, the sensitivity of a silver halide emulsion need not be enhanced excessively. Accordingly, the dye developer of the present invention provides a stable light-sensitive material.

Thirdly, the cyan color image by the present invention after processing exhibits an absorption in a longer wavelength region as compared with that of a conventional bis-azo cyan dye developer and the dye developer of the present invention provides a color diffusion transfer light-sensitive material excellent in color reproduction.

Fourthly, since the dye forming the cyan color image after processing has a larger extinction coefficient as compared with conventional anthraquinone cyan dye developers, the necessary optical density can be obtained by using a less amount of the dye developer of this invention.

Fifthly, the cyan dye developer of the present invention permits the chemical structure with ease to be modified to a slight extent. Therefore, desired photographic properties can easily be obtained.

Synthesis examples of the compounds of the present invention and Examples of their application to a light-sensitive material are given below. Unless otherwise indicated herein, all parts, percents ratios and the like are by weight.

SYNTHESIS EXAMPLE 1

Synthesis of Compound 1 a. Synthesis of 2-(2',5'-Dimethoxy-4'-nitrophenylazo)-4-isopropoxy-1-naphthol:

400 ml of water and 15 ml of a 35% hydrochloric acid aqueous solution were added to 11.2 g of 2,5-dimethoxy-4-nitroaniline and the mixture was cooled to 0° to 5°C uner stirring. To this was added a solution prepared by dissolving 3.5 g of sodium nitrite in 40 ml of water, to thereby conduct a diazotization. After the addition, the slow stirring was continued for 10 minutes. Then, the solution was neutralized to a pH of 6 using sodium acetate. Upon dropwise addition of this ice-cooled solution to a solution comprising 9.1 g of 4-isopropoxy-1-naphthol and 200 ml of ethanol at a temperature not higher than 5°C under stirring, crystals were formed. Additionally, the process for synthesizing this 4-isopropoxy-1-naphthol is described in detail in U.S. Pat. No. 3,022,354. After slowly stirring the mixture as such for 1 hour at a temperature not higher than 5°C, the mixture was filtered, and the filter cake was washed sufficiently with water, followed by drying to obtain 15 g of a crude product. This product was dissolved in 150 ml of benzene and 100 ml of methanol was added thereto, followed by cooling for crystallization. Thus, 12.3 g of dark purple, needle-like crystals of the above-mentioned compound having a melting point of 245° — 249°C was obtained.

b. Synthesis of 2-(2',5'-Dimethoxy-4'-aminophenylazo)-4-isopropoxy-1-naphthol:

200 ml of ethanol was added to 8.2 g of the compound obtained in (a) above and the mixture was warmed to 50°C under slow stirring. To this was gradually added dropwise a solution prepared by dissolving 19.2 g of sodium sulfide in 100 ml of water over a 20 minute period and, while maintaining the temperature at 50°C, slow stirring was continued for 1 hour and 30 minutes. Upon adding 1 liter of water, a crystals were precipitated. The thus precipitated crystals were filtered out, well washed with water and dried. Upon recrystallization from 200 ml of ethyl acetate, 7 g of the above-mentioned needle-like compound having a melting point of 186° to 187°C was obtained.

c. Synthesis of 1-{4'-[p-2'',5''-bis(Acetoxyphenethyl)]phenyl}-3-carbethoxy-4-[2''',5'''-dimethoxy-4''''-(4''''-isopropoxy-α-naphthol-2'''''-azo)-phenylazo]-5-pyrazolone:

12 g of the compound obtained in (b) above was dissolved in 150 ml of glacial acetic acid and diazotized with 32 ml of 1 N sodium nitrite at about 10°C.

Separately, 14 g of 1-[p-(2',5'-diacetoxyphenethyl)-phenyl]-3-carbethoxy-5-pyrazolone was dissolved in 200 ml of acetone and 500 ml of ethanol, followed by cooling to a temperature not higher than 5°C.

Additionally, a process for synthesizing this 1-[p-2',-5'-diacetoxyphenethyl)phenyl]-3-carbethoxy-5-pyrazolone is described in detail in Japanese Patent Publication No. 14064/66.

After cooling to a temperature not higher than 5°C, the foregoing diazo solution was gradually added thereto over a 20 minute period under stirring. Then, sodium acetate was added thereto in an amount sufficient to adjust the pH to about 7.0. After stirring the mixture as such for 2 hours at a temperature not higher than 5°C, the crystals precipitated were filtered out and well washed with water.

Further, the resulting crystals were washed several times with methanol using a total amount of 1 liter, and then dried. These crystals were dissolved in 300 ml of dimethylformamide. Upon cooling to crystallize, 17 g of the above-mentioned compound having a melting point of 263° to 267°C was obtained.

d. Synthesis of 1-(4'-Hydroquinonylethylphenyl)-3-carboxy-4-[2'',5''-dimethoxy-4''-(4''''-isopropoxy-α-naphthol-2'''-azo)-phenylazo]-5-pyrazolone:

15 g of the compound obtained in (c) above was suspended in 800 ml of ethanol and, after adding thereto a solution comprising 11 g of potassium hydroxide and 33 ml of water in vacuo, the mixture was heated to 60°C for 30 minutes. After cooling, 26 ml of a 35% hydrochloric acid aqueous solution was added to the vacuum system to precipitate crystals. These crystals were filtered out, well washed with water, and dried. Then, 100 ml of methanol was added thereto and the mixture cooled to precipitate crystals. Thus, 12 g of the above-mentioned compound having a melting point of 240° to 243°C was obtained.

When the resulting compound was dissolved in an organic solvent such as acetone and the absorption spectrum was measured, the compound exhibited a λ max of 640 mμ (the λ max being the wavelength at which the absorption reaches a maximum).

e. Conversion of Hydroquinone Moiety to Quinone:

14 g of the compound obtained in (d) above was refluxed together with 4 g of p-benzoquinone, 500 ml of dimethylformamide and 500 ml of ethylene dichloride for 5 hours over a steam bath. Upon distilling off the solvent, a tarry substance remained.

When 500 ml of water was added thereto and the mixture stired for a while, crystallization occurred. The crystals thus formed were filtered out, washed with a large amount of warm water, washed several times with methanol using 1 liter in total, and then dried.

This was dissolved in 200 ml of dimethylformamide, and 150 ml of methanol was added thereto. Upon cooling to precipitate crystals, a quinone derivative having a melting point of 235° to 245°C was obtained.

f. Synthesis of 1-(4'-Quinonylethylphenyl)-3-carboxy-4-[2'',5''-dimethoxy-4''-(1''''-acetoxy-4''''-isopropoxynaphthyl-2'''-azo)phenylazo]-5-pyrazolone:

8 g of the compound obtained in (e) above was refluxed for 7 hours over a steam bath together with 16 ml of isopropenyl acetate, 200 ml of ethylene dichloride and 0.1 ml of concentrated sulfuric acid.

After repeatedly washing the solution with water until the washing become neutral, the solution was dried over anhydrous sodium sulfate, followed by distilling off the solvent. Upon recrystallization from ethylene dichloride, 8 g of the above-mentioned compound having a melting point of 145° to 150°C ws obtained.

g. Synthesis of Compound 1:

8 g of the compound obtained in (f) above was dissolved in 500 ml of ethylene dichloride, and 2.8 g of 2,5-di-t-butylhydroquinone was added thereto. Upon stirring for 2 hours in a conventional manner, crystals were precipitated. These crystals were filtered out and washed several times with benzene using 500 ml in total. Recrystallization from acetone yielded 6 g of Compound 1 having a melting point of 189° to 191°C.

When 1.91 mg of the resulting compound was dissolved in 100 ml of acetone and the spectral absorption spectrum was measured, the compound exhibited a λ max of 545 mμ. On the other hand, when 1/10 volume of a 0.1N sodium hydroxide aqueous solution was added to the solution, measurement of the spectral absorption spectrum showed a λ max of 635 mμ. These two spectral absorption curves are shown in FIG. 1 by the solid line and a broken line, respectively.

SYNTHESIS EXAMPLE 2

Synthesis of Compound 2 a. Synthesis of 2-(2'-Methoxy-4'-nitrophenylazo)-4-isopropoxy-1-naphthol:

600 ml of water and 20 ml of a 35% hydrochloric acid aqueous solution were added to 12.8 g of 2-methoxy-4-nitroaniline and the mixture was cooled to 0° – 5°C under stirring. Then, a solution prepared by dissolving 4.8 g of sodium nitrite in 60 ml of water was gradually added thereto for diazotization. Stirring was continued as such for 10 minutes and the pH was adjusted to 6 using sodium acetate.

Upon dropwise addition of this ice-cooled solution to a solution comprising 12 g of 4-isopropoxy-1-naphthol and 280 ml of ethanol at a temperature of not higher than 5°C under stirring, a coupling reaction took place to precipitate crystals. Stirring was continued for 1 hour while maintaining the temperature at not higher than 5°C, followed by filtration. The filter cake was well washed with water, then dried.

This was dissolved in 100 ml of benzene, and 100 ml of methanol was added thereto. Upon cooling, 14 g of crystals having a melting point of 190° to 195°C was precipitated.

b. Synthesis of 2-(2'-Methoxy-4'-amino-phenylazo)-4-isopropoxy-1-naphthol:

200 ml of ethanol was added to 7.6 g of the compound obtained in (a) above and the mixture was heated to 50°C while slowly stirring.

To this was dropwise added a solution prepared by dissolving 19.2 g of sodium sulfide in 100 ml of water gradually over a 20 minute period and, while maintaining the temperature at 50°C, slow stirring was further continued for 1 hour and 30 minutes. Upon addition of 1 liter of water, crystals were precipitated.

The crystals precipitated were filtered out, well washed with water and dried. Upon recrystallization from 150 ml of ethyl acetate, 6 g of the above-mentioned compound having a melting point of 199 to 201°C was obtained.

c. Synthesis of 1-(4''-Hydroquinonylethylphenyl)-3-carboxy-4-[2''-methoxy-4''-(4''''-isopropoxy-α-naphthol-2'''-azo)phenylazo]-5-pyrazolone:

11 g of the compound obtained in (b) above and 14 g of 1-[p-(2',5'-diacetoxyphenethyl)phenyl]-3-carbethoxy-5-pyrazolone were coupled with each other and hydrolyzed in the same manner as in (c) and (d) in Synthesis Example 1 to obtain 10 g of the above-mentioned compound having a melting point of 234° to 238°C.

When this compound was dissolved in an organic solvent such as acetone, measurement of the absorption spectrum showed a λ max of 615 mμ.

d. Synthesis of Compound 2:

10 g of the compound obtained in (c) above was subjected to oxidation of the hydroquinone moiety, acetylation, and reduction of the quinone moiety to obtain 7 g of Compound 2 having a melting point of 171° to 175°C. When the absorption spectrum of this compound was measured by dissolving it in an organic solvent such as acetone, the λ max was determined to be 495 mμ.

The present invention will now be illustrated in greater detail by the following non-limiting examples of preferred embodiments of the present invention.

EXAMPLE 1

On a transparent cellulose triacetate film subbed with gelatin were coated, in sequence, the following layers to prepare Light-Sensitive Element. (I).

1. Cyan Dye Developer Layer:

1 part of the foregoing Compound 1, i.e., 1-(4'-hydroquinonylethylphenyl)-3-carboxy-4-[2'',5''-dimethoxy-4''-(1'''-acetoxy-4'''-isopropoxy-naphthyl-2'''-azo)phenylazo]-5-pyrazolone was dissolved in 2 parts of N,N-diethyllaurylamide and 4 parts of cyclohexanone. Then, this solution was emulsified and dispersed in a gelatin aqueous solution with the help of sodium n-dodecylbenzenesulfonate (dispersing agent) and coated at a coverage of 0.90 g/m² of the dye developer, 1.6 g/m² of gelatin and 1.8 g/m² of N,N-diethyllaurylamide.

2. Red-Sensitive Emulsion Layer:

A red-sensitive silver bromoiodide emulsion (containing 2 mol% silver iodide) spectrally sensitized with 3,3', 9-triethyl-5,5'-dichlorothiacarbocyanine iodide was coated at a coverage of 3.5 g/m² of silver and 4.0 g/m² of gelatin.

3. Protective Layer:

1 part of 4'-methylphenylhydroquinone was dissolved in a mixture of 1 part of tri-o-cresyl phosphate and 1.5 parts of ethyl acetate. Then, this solution was emulsified and dispersed in a gelatin aqueous solution with the help of sodium n-dodecylbenzenesulfonate, and coated at a coverage of 0.20 g/m² of 4'-methylphenylhydroquinone, 0.6 g/m² of gelatin and 0.20 g/m² of tri-o-cresyl phosphate.

Additionally, mucochloric acid was added to each layer as a hardener at a coverage of 0.03 g/m².

As a comparative sample for Light-Sensitive Element (I), Light-Sensitive Element (II) was prepared, which was the same as Light-Sensitive Element (I) except that the cyan dye developer layer was as follows.

1. Cyan Dye Developer Layer in Light-Sensitive Element (II):

For the purpose of comparison, 1 part of 1,4-[bis-γ-hydroquinonyl-2-methyl-propylamino]-5,8-dihydroxy-anthraquinone (comparative compound), described in U.S. Pat. No. 3,209,015, was dissolved in a mixture of 2.5 parts of N,N-diethyllaurylamide and 2.5 parts of cyclohexanone. Then, this solution was emulsified and dispersed in a gelatin aqueous solution with the help of sodium n-dodecylbenzenesulfonate, and coated at a coverage of 0.60 g/m² of the dye developer, 1.0 g/m² of gelatin and 1.2 g/m² of N,N-diethyllaurylamide.

Next, on a transparent polyethylene film were coated, in sequence, the following layers to prepare an image-receiving element.

1. Acidic Polymer Layer:

A 20% methyl ethyl ketone solution of maleic anhydridevinyl methyl ether (1:1 molar ratio) copolymer butyl half ester (mean molecular weight: about 100,000) was coated in a dry thickness of 20 μ.

2. Timing Layer:

1 part of 2-hydroxyethyl methacrylate was dissolved in a mixed solvent of 3 parts of acetone and 1 part of water, and coated in a dry thickness of 7 μ.

3. Image-Receiving Layer:

1 part of poly-4-vinyl pyridine, 2 parts of polyvinyl alcohol (saponification degree: 98 mol%; polymerization degree: 1800) and 1/20 part of 1-phenyl-5-mercaptotetrazole were dissolved in 150 parts of water containing ½ part of glacial acetic acid, and this solution was coated at a coverage of 3.2 g/m² of poly-4-vinyl pyridine, 3.2 g/m² of polyvinyl alcohol, and 0.16 g/m² of 1-phenyl-5-mercaptotetrazole.

Each of Light-Sensitive Elements (I) and (II) was subjected to an exposure of 20 C.M.S. from the support side using a tungsten light of a color temperature of 2854°K through an optical wedge and a red filter (Fuji Gelatin Filter, SC-62). Then, each of Light-Sensitive Elements (I) and (II) was superposed on an image-receiving element, and the following processing solution was spread therebetween in an amount of 1.4 cc per 100 cm² of the image-receiving element to conduct transfer development.

| Water | 100 cc |
|---|---|
| Potassium Hydroxide | 11.2 g |
| Hydroxyethyl Cellulose | 4.0 g |
| Benzotriazole | 3.5 g |
| Potassium Thiosulfate | 0.5 g |
| Lithium Nitrate | 0.5 g |
| Zinc Nitrate | 0.5 g |
| N-Benzyl-α-picolinium Bromide | 2.3 g |

After development-processing for about 2 minutes, the image-receiving element was delaminated and well washed with water. Thus, a cyan dye image was transferred to the image-receiving element according to the exposure amount.

The transmission density of the transferred cyan dye was measured using a red filter (using a densitometer, Model P2, made by the Fuji Photo Film Co., Ltd.). With Light-Sensitive Element (I), the Dmax and Dmin were 0.86 and 0.10, respectively, while, with Light-Sensitive Element (II), the Dmax and Dmin were 0.90 and 0.12, respectively.

Figure 2:
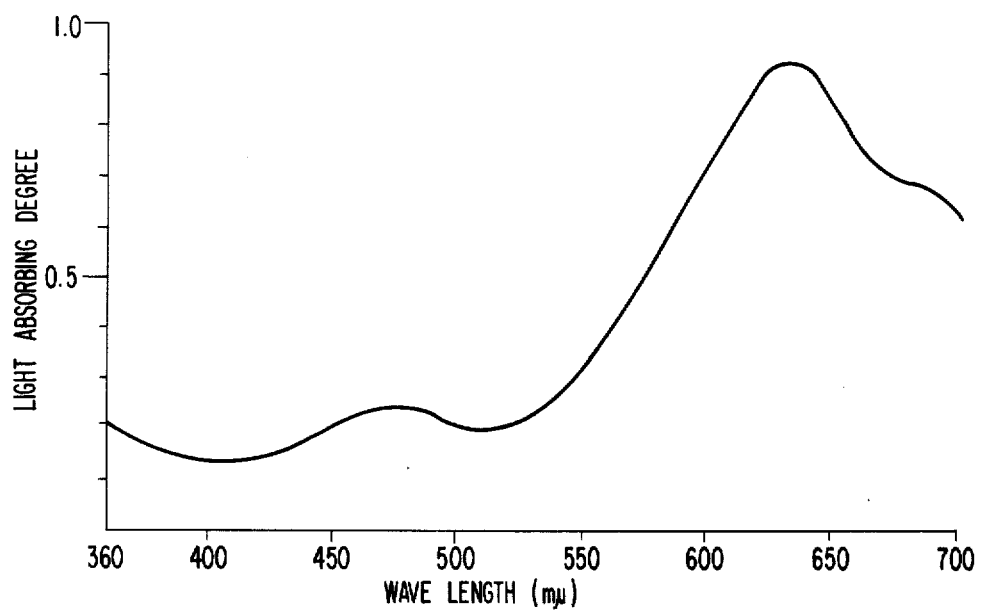
FIG. 2 shows the spectral absorption curve of Compound 1 after transfer development.

The spectral absorption of the dye image obtained by transferring from Light-Sensitive Element (I) to the image-receiving element through processing for 120 seconds and measured in terms of transmission density is shown in FIG. 2.

Then, each of Light-Sensitive Elements (I) and (II) was subjected to the same exposure as above from the opposite side to the support, and the same transfer development was conducted. The degree of reduction in sensitivity in the case of exposure from the support side was compared with that in the case of exposure from the opposite side to the support. With Light-Sensitive Element (I), the -Δlog E was 1.1, while, with Light-Sensitive Element (II), the -Δlog E was 2.4. Thus, it was shown that Light-Sensitive Element (I) underwent less reduction in sensitivity as compared with Light-Sensitive Element (II).

In order to compare the absorption of the dye developer layer contained in the light-sensitive element before processing, the spectral absorption of samples prepared by only coating each of the aforesaid dye developer on a gelatin-subbed cellulose triacetate was measured in terms of transmission density. The results thus obtained are shown in FIG. 3.

Figure 3:
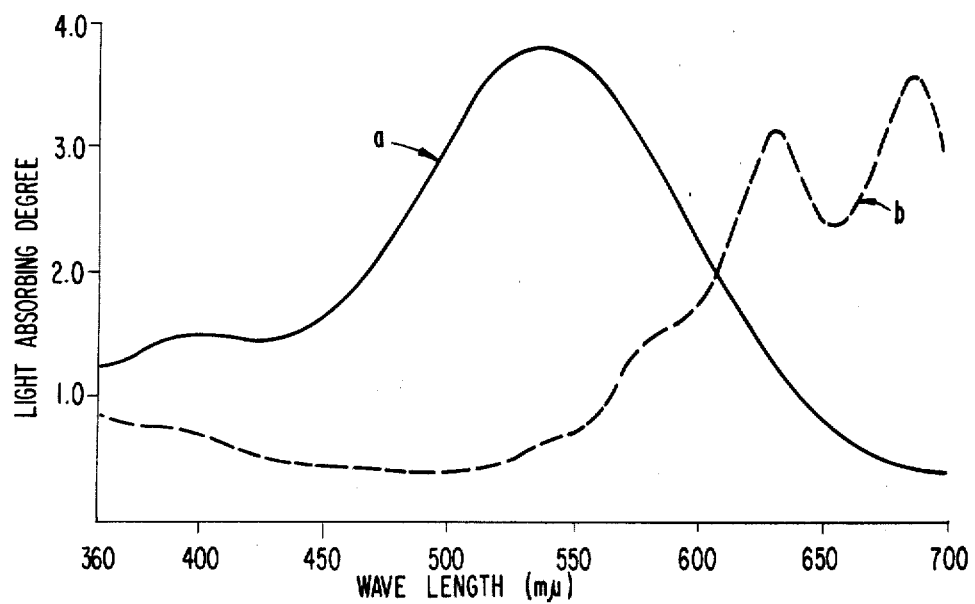
FIG. 3 is a graph comparatively showing the spectral absorption curve of Compound 1 in a light-sensitive material and that of a comparative compound, 1,4-[bis-γ-hydroquinonyl-α-methyl-propylamino]-5,8-dihydroxyanthraquinone, used in Example 1.

Curve a in FIG. 3 shows the spectral absorption curve of the dye developer layer containing Compound 1, while Curve b shows the spectral absorption curve of the dye developer layer containing the aforesaid comparative compound. Curve a shows a λ max of 540 mμ, while Curve b shows two split λ max peaks of 690 mμ and 634 mμ in a long wavelength region.

As is clear from this figure, it is seen that the absorption of Compound 1 is shifted to a shorter wavelength region as compared with that of the comparative dye developer without seriously damaging the spectral sensitivity of a red-sensitive emulsion associated therewith.

EXAMPLE 2

The absorption of a light-sensitive element prepared by using Compound 4 in place of Compound 1 used in Example 1 was found to be shifted to a shorter wavelength region before processing and, after processing, the absorption of the compound in an image-receiving element was restored to 635 mμ in λ max. The degree of reduction in sensitivity when exposed from the support side of the light-sensitive element, measured in the same manner as in Example 1, was a -Δlog E, of 0.8 which was lower than the case of using the comparative compound.

EXAMPLE 3

On a gelatin-subbed transparent cellulose triacetate film were coated, in sequence, the following layers to prepare a light-sensitive element.

1. Yellow Dye Developer Layer:

1 part of 3-acetoxy-3-(2-coumaronyl)-2-[2-methyl-5-(2-hydroquinonylethyl)phenylazo]acrylonitrile was dissolved in 1 part of N,N-diethyllaurylamide and cyclohexanone, emulsified and dispersed in a gelatin aqueous solution with the help of sodium n-dodecylbenzenesulfonate, and coated at a coverage of 1.5 g/m² of the dye, 1.7 g/m² of gelatin, and 1.5 g/m² of N,N-diethyllaurylamide.

2. Blue-Sensitive Emulsion Layer:

A blue-sensitive silver bromoiodide emulsion (containing 2 mol% silver iodide) was coated at a coverage of 2.3 g/m² of silver and 1.7 g/m² of gelatin.

3. Interlayer

A layer of colloidal silver coated at a coverage of 0.3 g/m² of silver and 3.5 g/m² of gelatin.

4. Magenta Dye Developer Layer:

1 part of 4-methoxyethoxy-2-[4-(2-hydroquinonylethyl)phenylazo]naphthalene-1-acetate was dissolved in 1 part by weight of N,N-diethyllaurylamide and 4 parts by weight of cyclohexanone, emulsified and dispersed in a gelatin aqueous solution with the help of sodium n-dodecylbenzenesulfonate, and coated at a coverage of 1.0 g/m² of the dye, 1.3 g/m² of gelatin and 1.0 g/m² of N,N-diethyllaurylamide.

5. Green-Sensitive Emulsion Layer:

A green-sensitive silver bromoiodide emulsion layer (containing 2 mol% silver iodide) spectrally sensitized with a sensitizing dye, 3,3',9-triethyl-5,5'-diphenyloxacarbocyanine bromide, was coated at a coverage of 1.0 g/m² of silver and 0.8 g/m² of gelatin.

6. Interlayer:

A gelatin layer coated at a coverage of 3.5 g/m².

7. Cyan Dye Developer Layer:

1 part of the dye (Compound 1) was dissolved in 2 parts of N,N-diethyllaurylamide and 4 parts of cyclohexanone, emulsified and dispersed in a gelatin aqueous solution, and coated at a coverage of 0.50 g/m² of said dye, 1.2 g/m² of gelatin and 0.50 g/m² of N,N-diethyllaurylamide.

8. Red-Sensitive Emulsion Layer:

A silver bromoiodide emulsion layer (containing 2 mol% silver iodide) spectrally sensitized with a red-sensitive sensitizing dye, 3,3',9-triethyl-5,5'-dichlorothiacarbocyanine iodide, was coated at a coverage of 0.50 g/m² of silver and 0.37 g/m² of gelatin.

9. Protective Layer:

1 part of 4'-methylphenylhydroquinone was dissolved in 1 part by weight of tri-o-cresyl phosphate and 1.5 parts of ethyl acetate, emulsified and dispersed in a gelatin aqueous solution using sodium n-dodecylbenzene sulfonate as a dispersing aid, and coated at a coverage of 0.45 g/m² of 4'-methylphenylhydroquinone, 1.3 g/m² of gelatin and 0.45 g/m² of tri-o-cresyl phosphate.

Additionally, mucochloric acid was added to each layer as a hardener at a coverage of 0.03 g/m².

Next, on a transparent polyethylene film were coated, in sequence, the following layers to prepare an image-receiving element.

1. Acidic Polymer Layer:

A 20% methyl ethyl ketone solution of the butyl half ester of a maleic anhydride-vinyl methyl ether (1:1 molar ratio) copolymer (mean molecular weight: 100,000) was coated in a dry thickness of 40 μ.

2. Timing Layer:

1 part of 2-hydroxyethyl methacrylate was dissolved in a mixed solvent comprising 3 parts by weight of acetone and 1 part by weight of water, and coated in a dry thickness of 14 μ.

3. Image-Receiving Layer:

The same as in Example 1.

Then, the thus prepared light-sensitive element was wedge-exposed from the support side using red, green and blue lights, respectively. Then, the following processing solution was spread between the light-sensitive element and the image-receiving element in a proportion of 1.0 cc per 100 cm² of the image-receiving element to effect transfer development.

| Processing Solution | | |
|---|---|---|
| Water | 100 | cc |
| Calcium Hydroxide | 11.2 | g |
| Hydroxyethyl Cellulose | 3.5 | g |
| Benzotriazole | 1.5 | g |
| N-Phenethyl-α-picolinium Bromide | 2.0 | g |
| Titanium Dioxide | 50 | g |

5 Minutes after the development processing, red, green and blue colors were observed to appear from the support side of the image-receiving element without delaminating the image-receiving element.

EXAMPLE 4

On a gelatin-subbed transparent cellulose triacetate were coated, in sequence, the following layers to prepare Light-Sensitive Element (III).

1. Cyan Dye Developer-Containing Red-Sensitive Emulsion Layer:

The above described Compound 1 was emulsified and dispersed in the same manner as with Light-Sensitive Element (I) in Example 1. Then, the resulting emulsion was mixed with a red-sensitive silver halide emulsion and coated at a coverage of 1.0 g/m² of silver, 0.6 g/m² of the dye developer, 2.1 g/m² of gelatin and 1.2 g/m² of N,N-diethyllaurylamide.

2. Protective Layer:

The same as in Example 1.

Additionally, mucochloric acid was added to each layer as a hardener at a coverage of 0.03 g/m².

As a comparative sample for Light-Sensitive Element (III), Light-Sensitive Element (IV) was prepared (the same as Light-Sensitive Element (III) except for using the following cyan dye developer) by coating an emulsion containing the same dye developer as used for Light-Sensitive Element (II) in Example 1 at a coverage of 1.0 g/m² of silver, 0.4 g/m² of the dye developer and 0.8 g/m² of N,N-diethyllaurylamide.

Light-Sensitive Elements (III) and (IV) were subjected to an exposure of 20 C.M.S. through both an optical wedge and a red filter (Fuji Gelatin Filter, SC-62) using a tungsten light of a color temperature of 2854°K. Then, each of Light-Sensitive Elements (III) and (IV) was superposed on an image-receiving element (the same as in Example 3), and a processing solution (the same as used in Example 3) was spread therebetween in a proportion of 1.0 cc per 100 cm² of the image-receiving element to conduct transfer development. Five minutes after the development-processing, it was observed from the support side of the image-receiving element without delamination of the image-receiving element that a cyan dye image was transferred thereto in proportion to the exposure amount.

The reflection density of the transferred cyan dye was measured using a red filter. With Light-Sensitive Element (III), the Dmax and Dmin were 2.10 and 0.28, respectively while, with Light-Sensitive Element (IV), the Dmax and Dmin were 2.28 and 0.34, respectively.

Between Light-Sensitive Elements (III) and (IV), these values of Dmax and Dmin were almost the same and are supposed to satisfy the values required for Dmax and Dmin as a light-sensitive material. Since light-sensitive elements showin almost the same Dmax were obtained, the sensitivity difference between these two samples was compared with each other. As a result, it was found that Light-Sensitive Element (III) containing both Compound 1 and the red-sensitive emulsion was more sensitive than Light-Sensitive Element (IV) containing both the comparative cyan dye developer and the red-sensitive emulsion by 1.3 in terms of log E value. From this, it is seen that to shift the hue of the dye developer associated with the red-sensitive emulsion to a shorter wavelength region as with Compound 1 serves to prevent a reduction in sensitivity of the red-sensitive emulsion.

From the above description, it can be seen that the use of the dye developer of the present invention reduces the reduction of spectral sensitivity of a red-sensitive emulsion when it is mixed with the cyan dye developer.

While the invention has been described in detail and with reference to specific embodiments thereof, it will be apparent to one skilled in the art that various changes and modifications can be made therein without departing from the spirit and scope thereof.

What is claimed is:

1. In a light-sensitive material comprising a support having thereon a blue-sensitive silver halide emulsion layer and a yellow dye developer associated therewith, a green-sensitive silver halide emulsion layer and a magenta dye developer associated therewith, and a red-sensitive silver halide emulsion layer and a cyan dye developer associated therewith, the improvement characterized in that said cyan dye developer comprises a compound represented by the following general formula (I):

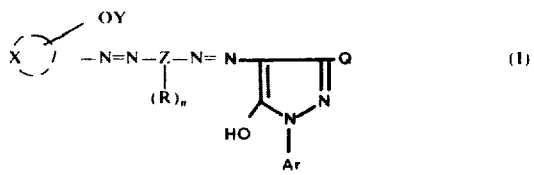

wherein X represents the atoms necessary for completing a monocyclic or polycyclic aromatic group; Y represents an acyl group having 1 to 4 carbon atoms; Ar and Z each represents a phenyl nucleus or a naphthalene nucleus, with Ar being connected either directly or through a divalent atom or group to a polyhydric phenol moiety having a silver halide developing action; R represents an alkyl group or an alkoxy group; n represents an integer of 0 to 4; and Q represents

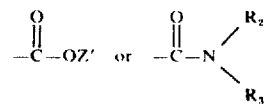

wherein Z' represents a hydrogen atom or an alkyl group, $R_2$ and $R_3$ each represents a hydrogen atom or an aliphatic group, or $R_2$ and $R_3$ can combine to form a divalent aliphatic group.

2. The light-sensitive material of claim 1, wherein said cyan dye developer is positioned in front of of said red-sensitive silver halide emulsion layer with respect to incident light of exposure.

3. The light-sensitive material of claim 1, wherein said cyan dye developer is present in said red-sensitive silver halide emulsion layer.

4. The light-sensitive material of claim 1, wherein in the formula (I) cyan dye developer the atoms represented by X form a naphthalene nucleus, a benzene nucleus, a coumarone nucleus, an indole nucleus, a benzothiophene nucleus, a quinoline nucleus, an oxazole nucleus, a thioazole nucleus, a naphthyridine nucleus, or a derivative thereof substituted with one or more of an alkyl group, a sulfo group, an alkoxy group, an aryl group, an aryloxy group, an amino group, a carboxy group, an alkylamino group, an arylamino group, a hydroxyl group, a cyano group, an alkylamido group, and an arylsulfonamido group; wherein said divalent
  atom or group connecting said Ar to said polyhydric phenol moiety having a silver halide developing action is an alkylene group, -O-, -S-, -SO₂-, CO-, -COCH₂- or -CH₂CH₂S-; wherein R represents an alkyl group or an alkoxy group, each having 1 to 4 carbon atoms; wherein the alkyl group for Z' is an alkyl group having 1 to 12 carbon atoms; wherein the aliphatic group for R₂ and R₃ has 1 to 9 carbon atoms and is an alkyl group, an alkylcarbamoyl group or a carbamoyl group; and wherein said divalent aliphatic group for R₂ and R₃ is -(CH₂)₅- or -(CH₂)₂-O- (CH₂)₂-.

5. The light-sensitive material of claim 1, wherein said cyan dye developer is 1-[4'-hydroquinonylethyl)-phenyl]-3-carboxy-4-[2'',5''-dimethoxy-4''-(1'''-acetoxy-4''''-isopropoxynaphthyl-2'''-azo) phenylazo]-5-pyrazolone, 1-[4'-(hydroquinonylethyl)phenyl]-3-carboxy-4-[3''-methoxy-4''-(1''''-acetoxy-4''''-isopropoxynaphthyl-2'''-azo) phenylazo]-5-pyrazolone, 1-[4'-(hydroquinonylethyl)phenyl]-3-carboxy-4-[2''-methoxy-4''-(1''''-acetoxy-4''''-isopropoxynaphthyl-2'''-azo) phenylazo]-5-pyrazolone, 1-[4'-(hydroquinonylethyl)phenyl]-3-carboxy-4-[2'',5''-dimethoxy-4''-{1''''-acetoxy-4''''-[(2-methoxy)ethoxy]-naphthyl-2'''-azo}phenylazo]-5-pyrazolone, 1-[4'-hydroquinonylethyl)-phenyl]-3-ethoxycarbonyl-4-[2'λ',5''-dimethyl-4''-(1''''-chloroacetoxy-4''''-isopropoxynaphthyl-2'''-azo)phenylazo]-5-pyrazolone, 1-[4'-hydroquinonylethyl)phenyl]-3-methoxycarbonyl-4-[2'',5''-diethoxy-4''-(1''''-acetoxy-4''''-[(2-ethoxy)ethoxy]naphthyl-2'''-azo)phenylazo]-5-pyrazolone, 1-[3'-hydroquinonylmethyl)phenyl]-3-carboxy-4-[2'',5''-dimethoxy-4''-(1''''-acetoxy-4''''-isopropoxynaphthyl-2'''-azo)phenylazo]-5-pyrazolone, 1-[2'(hydroquinonyl)phenyl]-3 -carboxy-4-[2'',5''-dimethoxy-4''-(1''''-acetoxy-4''''-isopopoxynaphthyl-2'''-azo)-phenylazo]-5-pyrazolone, 1-[4'-(hydroquinonylethyl)-phenyl]-3-carbamoyl-4-[2'',5''-dimethoxy-4''-(3'''-acetoxybenzo[b]-thienyl-2'''-azo)phenylazo]-5-pyrazolone, or 1-[4'(hydroquinonyl-ethyl)phenyl]-3-N,N-cyclopentamethylenecarbamoyl-4-[2',5'-dimethoxy-4'-(6''-methoxyacetoxyquinolyl-5''-azo)-phenylazo]-5-pyrazolone.

6. The light-sensitive material of claim 1, wherein said cyan dye developer of the general formula (I) is 1-[4'-hydroquinonylethyl)phenyl]-3-carboxy-4-[2'',5''-dimethoxy-4''-(1''''-acetoxy-4''''-isopropoxynaphthyl-2'''-azo)phenylazo]-5-pyrazolone.

7. The light-sensitive material of claim 1, wherein said cyan dye developer of the general formula (I) is 1-[4'-hỳdroquinonylethyl)phenyl]-3-carboxy-4-''2'',5''-dimethoxy-4''-{1''''-acetoxy-4''''-[(2-methoxy)ethoxy]naphthyl-2'''-azo}phenylazo]-5-pyrazolone.

8. In a photographic unit for the diffusion transfer process comprising
  a. a light-sensitive element comprising a support having thereon at least one silver halide emulsion layer and a cyan dye developer associated therewith,
  b. an image-receiving element comprising (1) a support, (2) an image-receiving layer for receiving dyes transferred on development of the light-sensitive element, and (3) a layer containing an alkali-neutralizing agent positioned between said support for said image-receiving element and said image-receiving layer; and
  c. an alkaline liquid processing composition for spreading between said light-sensitive element and said image-receiving element for development of said silver halide in said light-sensitive element and transfer of dye images from said light-sensitive element to said image-receiving element; the improvement wherein the cyan dye developer comprises a compound represented by the following general formula (I);

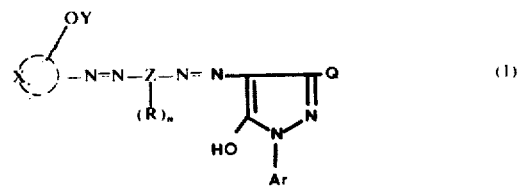

wherein X represents the atoms necessary for completing a monocyclic or polycyclic aromatic group; Y represents an acyl group having 1 to 4 carbon atoms; Ar and Z each represents a phenyl nucleus or a naphthalene nucleus, with Ar being connected either directly or through a divalent atom or group to a polyhydric phenol moiety having a silver halide developing action; R represents an alkyl group or an alkoxy group; n represents an integer of 0 to 4; and Q represents

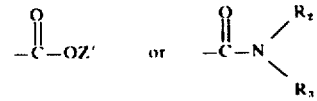

wherein Z' represents a hydrogen atom or an alkyl group, R₂ and R₃ each represents a hydrogen atom or an aliphatic group, or R₂ and R₃ can combine to form a divalent aliphatic group.

9. The photographic unit of claim 8, wherein said image-receiving layer includes a mordanting agent having a poly-4-vinyl pyridine structure.

10. The photographic unit of claim 8, wherein said at least one silver halide emulsion layer is shielded from light by a light-intercepting agent.

11. The photographic unit of claim 10, wherein said light-intercepting agent is carbon powder.

12. The photographic unit of claim 8, wherein said processing composition is retained in a rupturable container.

13. The photographic unit of claim 12, wherein said processing composition contains a light-reflecting agent.

14. The photographic unit of claim 13, wherein said light-reflecting agent is titanium dioxide.

* * * * *